United States Patent [19]

Barthell et al.

[11] 4,179,367

[45] Dec. 18, 1979

[54] THICKENING URINARY AND INTESTINAL TRACT EXCREMENT

[75] Inventors: Eduard Barthell; Otto Schmid, both of Krefeld, Fed. Rep. of Germany

[73] Assignee: Chemische Fabrik, Bakerpfad, Fed. Rep. of Germany

[21] Appl. No.: 876,824

[22] Filed: Feb. 10, 1978

[30] Foreign Application Priority Data

Feb. 14, 1977 [DE] Fed. Rep. of Germany ....... 2706135

[51] Int. Cl.² .................... C02B 1/14; B01D 15/00
[52] U.S. Cl. ................................. 210/41; 128/283; 128/295; 260/29.6 H; 260/42.29; 260/42.52
[58] Field of Search ............... 128/283, 295, 296, 284; 526/14; 252/259.5, 194, 316; 260/42.29, 42.48, 42.52; 210/24, 41

[56] References Cited

U.S. PATENT DOCUMENTS

| | | | |
|---|---|---|---|
| 3,354,084 | 11/1967 | Katzer | 260/42.29 |
| 3,980,663 | 9/1976 | Gross | 526/14 |
| 4,051,086 | 9/1977 | Reid | 128/296 |
| 4,056,502 | 11/1977 | Gross | 526/14 |
| 4,059,552 | 11/1977 | Zweigle et al. | 128/284 |
| 4,076,921 | 2/1978 | Stol et al. | 128/296 |
| 4,090,013 | 5/1978 | Ganslaw et al. | 128/284 |

FOREIGN PATENT DOCUMENTS 982082  1/1976  Canada ................................. 260/42.29

*Primary Examiner*—Lewis T. Jacobs
*Attorney, Agent, or Firm*—Sprung, Felfe, Horn, Lynch & Kramer

[57] ABSTRACT

Urinary and intestinal tract excrement, such as from a stoma patient, is thickened by admixture with a cross-linked water-swellable polymer, preferably including (meth)acrylic acid, nitrile and/or amide units. A hydrophilic adsorption agent such as silicic acid may also be included along with perfume materials, binders and/or enzyme inhibitors. By thickening, it prevents sloshing of the contents, reduces odors and facilitates ultimate disposal.

7 Claims, No Drawings

THICKENING URINARY AND INTESTINAL TRACT EXCREMENT

The invention relates to an agent for thickening the contents of the intestine or urine after the excretion thereof from the human body, especially after excretion through artificial intestinal and/or urinary passages for patients having artificial intestinal and/or urinary passages, (so-called stoma patients).

As is well known, stoma patients who have been provided with an intestinal passage by surgery, empty the contents of the intestine into containers, usually bags made of a plastic material, which are attached directly to the artificial intestinal passage and seal this off as tightly as possible. The same applies to patients who, owing to a urinary fistula or for other reasons, have been given an artificial urinary passage. This group of patients has to cope with the problem that the excretion emptied into the collecting bag is frequently liquid, and, moreover, develops an unpleasant smell owing to the increasing formation of gas, as a result of which both the patient himself and those in the area surrounding him are considerably disturbed and inconvenienced. In particular the liquid character of the excretion products, as in the case of urine and intestinal contents of a very thin consistency, is extremely irksome, as the liquid slops around in the discharge bag when the patient moves.

For this increasing proportion of stoma patients, it is extremely desirable for the excreted excrement (contents of the intestine or urine) to be thickened by simple measures to a consistency which corresponds approximately to the consistency of the intestinal excrement of a normal person. It is also desirable for odors to be substantially eliminated together with this thickening process, in order as far as possible to exclude the otherwise unavoidable inconvenience of smell.

The problem described, which has so far remained unsolved, is solved by the invention in a satisfactory and extremely simple manner.

The solution comprises bringing into contact, in the collecting container, the excretion products immediately after they have left the body, with a special thickening agent based on a polymer which, as a result of cross-linking, is no longer soluble in water but only swellable therein. Surprisingly, it was discovered that the consistency of the excretion products (contents of the intestine and urine) could be altered with this thickening agent, and that from liquids, such as urine, or thin intestinal contents, a viscous composition is obtained which approximates in consistency the intestinal excreta of a normal person.

The invention accordingly relates to thickening agents for the excreted contents of the intestine and/or urine, which are characterized in that they contain at least one cross-linked polymer that, in water, merely swells. The thickening agent is particularly suitable for intestinal contents and/or urine excreted through an artificial intestinal and/or urinary passage.

Polymers based on acrylic acid derivatives are preferred, particularly those based on acrylic and methacrylic acid, acrylamide and acrylonitrile.

Cross-linked homopolymers of salts of acrylic acid or methacrylic acid, e.g. the alkali metal acrylates and alkali metal methacrylates are especially suitable, in particular the corresponding sodium salts or mixtures or polymers from acrylates and methacrylates.

Also suitable are copolymers of acrylic acid derivatives, acrylic acid, methacrylic acid, acrylamide, methacrylamide and acrylonitrile, either with each other or with vinyl pyrrolidone. Among these, copolymers of acrylic acid and methacrylic acid and copolymers of acrylic acid or methacrylic acid with acrylamide, methacrylamide and acrylonitrile are especially preferred. Mixtures of different copolymers may, of course, be used.

Examples of cross-linked polymers which may be used in accordance with the invention are:

(1) Homopolymers based on
   sodium acrylate
   sodium methacrylate
   acrylamide
   vinyl pyrrolidone (2) Copolymers based on
   sodium acrylate and acrylate acid
   sodium acrylate and sodium methacrylate
   sodium acrylate and acrylamide
   sodium methacrylate and acrylamide
   sodium acrylate and acrylonitrile
   sodium methacrylate and acrylonitrile
   vinyl pyrrolidone and acrylonitrile
   acrylamide and acrylonitrile, especially those containing a major amount by weight of (meth)acrylic acid, amide or nitrile units.

Suitable cross-linking agents for polymers of classes (1) and (2) are olefinic monomers which are at least bifunctional, such as methylene bisacrylamide, divinyl benzene, trisallyl cyanurate, trisallyl phosphate etc., which, relative to the weight of the monomers according to 1 and 2, are used in proportions of about 0.05 to 3.00% by weight, especially in proportions of about 0.1 to 1.0% by weight. The preparation of the corresponding cross-linked polymers by radical or redox polymerization is known.

The agent according to the invention is introduced into the empty bag in a suitable measured quantity which is sufficient to thicken adequately the entire contents of a stoma bag. To facilitate the addition of the measured quantity and handling by the patient, the agent according to the invention is advantageously used in the form of tablets; it may, however, be introduced in a different form, for example, in powdered or granulated form.

Surprisingly, the action of the polymer according to the invention is distinctly improved by the incorporation of a hydrophilic adsorption agent; whereas the polymer according to the invention alone converts the liquid excretion products into a soft, flowable gel, a polymer containing an hydrophilic adsorption agent has the effect of converting the liquid excretion products into a stiff, non-flowable, structured gel. Because of its consistency, the formation of such a gel is especially desirable and thus represents a considerable improvement over the still soft, flowable gel obtained by thickening with the polymer alone.

The desired result of a so-called stiff gel can be achieved by the addition to the polymeric thickening agent of even comparatively small proportions of the hydrophilic adsorption agent. Advantageously, the ratio by weight of polymer component to adsorption agent lies within the range of about 2:0.2 to 2:1, a range of about 2:0.5 to 3:1 being preferred. For practical purposes, the agent according to the invention contains from about 10 to 30% by weight of hydrophilic adsorption agent, relative to the total amount of polymer plus adsorption agent.

The synthetic silicic acids produced according to different, known methods, e.g. the known, pyrolytically produced silicic acids, which may be obtained commercially under the name "Aerosils" have proved just as suitable as adsorption agents as the finely divided silicic acids produced by precipitation of the colloidal solutions from water glass.

The agent according to the invention meets the requirements made of such a product, i.e., it is well-tolerated by the skin, is non-sensitizing and cannot be broken down by enzymes.

Although the thickening agent according to the invention is especially suitable for thickening urine or the contents of the intestine that has been excreted through artificial intestinal and/or urinary passages, and the thickening agent according to the invention is thus particularly suitable for so-called stoma patients, the invention is not restricted to the thickening of the contents of the intestine and/or urine excreted through artificial passages, and thus is not restricted to the group of stoma patients. On the contrary, the invention has been described only in conjunction with the particularly preferred application of the agent according to the invention with such stoma patients. Apart from this, the invention is generally suitable for thickening human excrement in portable toilet systems, in which excrement has first to be stored before being disposed of. The undesirable slopping backwards and forwards of the excrement collected and the annoyance caused by the smell thereof is also a problem with toilets of this kind installed in vehicles. In this case, too, it is highly desirable to thicken the excrement, especially to convert it into a non-flowable, stiff, even crumbly product, as not only its transport, but also its disposal, is thereby facilitated and annoyance caused by smell is eliminated.

To reduce annoyance caused by smell, besides the polymer and, if desired, the hydrophilic adsorption agent, perfume materials may be incorporated with the agent according to the invention in a quantity of approximately 0.1 to 1.0% by weight, based on the polymer plus hydrophilic adsorption agent, (if any). In the case where the agent according to the invention is used in compressed form, it advantageously contains a binder in an amount from approximately 1 10.0% by weight, based on the polymer and, if present, the hydrophilic agent. Furthermore, the agent according to the invention may contain enzyme inhibitors (such as allantoin, silver salts) in an amount of about 0.0001 to 0.01% by weight, based on the total of polymer plus hydrophilic adsorption agent (if any), for example $Ag^+$ for ureases. If required, in addition to the additives mentioned above, disinfecting agents may be added in the customary quantities. Examples of perfume materials include synthetic rose oil, synthetic oil of neroli, sandalwood oil and cedar oil. Suitable binders include starches, high molecular weight ethylene oxides and inorganic products, such as bentonite or talc.

The invention also provides a process for thickening human excrement, such as the contents of the intestine and/or urine, in which the excretion products, especially excretion products that have been excreted through artificial intestinal and/or urinary passages, are brought into contact in a collecting container with a sufficient quantity of a thickening agent to convert them into a gel, preferably a stiff, non-flowable, structured gel, which thickening agent contains a cross-linked polymer which is no longer soluble but merely swellable in water, optionally together with a hydrophilic adsorption agent, and other additives, such as, for example, perfume materials, binders, and enzyme inhibitors.

The thickening agent is advantageously introduced into the collecting container before use, either in powdered form or in the form of a compressed substance, i.e. a tablet.

The following advantages are described in relation to the preferred use of the thickening agent for stoma patients. As already mentioned, however, the invention is not limited thereto. The advantages described, such as rapid action and easy liquefaction of the resulting gel, apply equally to other applications of the invention.

In addition to the advantages already mentioned, namely conversion into the solid state of a liquid frequently felt to be troublesome, which the patient has to carry around with him externally against his body, and the substantial elimination of the annoyance caused by the smell by almost completely controlling the odor, a further advantage of the agent according to the invention is its rapid action. The polymer component and hydrophilic adsorption agent (if any) swell within a few minutes, whereas customary thickening agents, e.g. alginates or cellulose derivatives, which also have the advantage that they are broken down by enzymes, take a considerably longer time to swell. Another advantage of the agent according to the invention is the ease with which it can be measured out by the user, who may himself select the reqired amount, which may, for example, vary between 2 and 5% by weight according to his own needs. Finally, another advantage of the agent according to the invention is that the solid gel can be so liquefied by adding water that the emptying of the full bag is considerably facilitated. Another advantage is the universal application of the agent according to the invention not only for the contents of the intestine but also for urine. Finally, an advantage of converting the substantially liquid excretion products into a consolidated state is that such a consolidated product does not come into contact with the skin in the region around the artificial body passage to the same extent as the corresponding unthickened liquid. By this means, the risk of inflammation caused by faeces or urine is very strongly reduced. Depending on the type and nature of the excrement to be thickened, from 1 to 5 g of the polymer alone or from 1 to 4 g of the combination of polymer and adsorption agent will generally be sufficient to cause effective thickening of 100 ml of excrement. Of course, the amount of polymer and adsorption agent necessary to thicken the excrement to a soft flowable gel or to a stiff gel is dependent to some extent on the type of polymer and the type of adsorption agent.

The following examples illustrate the invention:

EXAMPLE 1

100 g of urine or thin stools are added to 5 g of cross-linked polyacrylate in a polyethylene bag. (The polyacrylate is one prepared by polymerization of 100 parts of sodium acrylate with 0.1 part of methylene bisacrylamide in 30% strength aqueous solution by initiation with potassium persulphate at room temperature. With the formation of a stiff polymer gel, the temperature rises to 97° C. The gel is comminuted, dried and ground in the customary manner.)

After about 10 minutes, the contents of the bag have been transformed into a viscous gel.

EXAMPLE 2

100 ml of urine or thin stools are introduced into a polyethylene bag containing 3 g of a cross-linked polyacrylate made as described in Example 1 and 1 g of pyrolytically prepared silicic acid (Aerosil 200 manufactured by the firm of DEGUSSA) in powder or tablet form.

After about 10 minutes the contents of the bag have been transformed into a gel having a crumbly structure.

EXAMPLE 3

100 ml of urine or thin stools are added to 5 g of cross-linked polyacrylate in a polyethylene bag. (The polyacrylate is one prepared by polymerization of a 30% strength aqueous solution of sodium acrylate and acrylic acid in a mixing ratio such that the pH-value of the solution of the copolymer formed is 5.0, with the addition of 0.1% of methylene bisacrylamide, based on the solids content of the solution, and with initiation with potassium persulphate at room temperature. The temperature rises to 97° C. with the formation of a stiff polymer gel. The gel is comminuted, dried and ground in the customary manner.) After about 10 minutes, the contents of the bag have been transformed into a viscous gel.

EXAMPLE 4

100 ml of urine or thin stools are introduced into a polyethylene bag containing 3 g of cross-linked polyacrylate made as described in Example 3 and 1 g of pyrolytically obtained silicic acid (Aerosil 200 manufactured by the firm of DEGUSSA) in powder or tablet form.

After about 10 minutes the contents of the bag have been transformed into a gel having a crumbly structure.

It will be appreciated that the instant specification and examples are set forth by way of illustration and not limitation, and that various modifications and changes may be made without departing from the spirit and scope of the present invention.

What we claim is:

1. A method of thickening urinary tract and intestinal excrement comprising mixing said excrement with about 1 to 5 grams of a cross-linked water-swelling polymer per 100 ml of excrement and with about 0.1–0.5 parts of a hydrophilic adsorption agent per part by weight of polymer.

2. A method according to claim 1, wherein the polymer comprises units of at least one of acrylic acid, methacrylic acid, acrylamide, methacrylamide, acrylonitrile and methacrylonitrile.

3. A method according to claim 2, wherein the polymer comprises units of at least one acrylic acid and methacrylic acid in acid or salt form.

4. A method according to claim 2, wherein the polymer comprises units of one of the recited monomers plus units of vinyl pyrrolidone or a second of the recited monomers.

5. A method according to claim 2, wherein the polymer comprises units of at least one of acrylic acid and methacrylic acid plus units of at least one of acrylamide, methacrylamide and acrylonitrile.

6. A method according to claim 1, wherein the adsorption agent comprises silicic acid.

7. A method according to claim 1, wherein the polymer is first supplied to a container to which the excrement is subsequently supplied.

* * * * *